US00RE34998E

United States Patent [19]

Langerman

[11] E Patent Number: Re. 34,998

[45] Reissued Date of Patent: Jul. 18, 1995

[54] "SPARE PARTS" FOR USE IN OPHTHALMIC SURGICAL PROCEDURES

[76] Inventor: David W. Langerman, c/o Langerman Eye Institute 99 Dutch Hill Plz., Orangeburg, N.Y. 10962

[21] Appl. No.: 76,984

[22] Filed: Jun. 15, 1993

Related U.S. Patent Documents

Reissue of:

[64] Patent No.: 4,888,016
Issued: Dec. 19, 1989
Appl. No.: 154,196
Filed: Feb. 10, 1988

[51] Int. Cl.[6] ..... A61F 2/14; A61F 2/16

[52] U.S. Cl. ..... 623/6; 623/4; 623/5; 623/66; 606/107; 606/151

[58] Field of Search ..... 623/4–6, 623/66; 606/107, 151

[56] References Cited

U.S. PATENT DOCUMENTS

| | | | |
|---|---|---|---|
| 4,141,973 | 2/1979 | Balazs | 424/180 |
| 4,253,199 | 3/1981 | Banko | 623/6 |
| 4,402,579 | 9/1983 | Poler | 623/6 |
| 4,452,776 | 6/1984 | Refojo | 623/4 X |
| 4,487,865 | 12/1984 | Balazs et al. | 524/29 |
| 4,556,998 | 12/1985 | Siepser | 623/6 |
| 4,582,865 | 4/1986 | Balazs et al. | 524/29 |
| 4,608,049 | 8/1986 | Kelman | 623/6 |
| 4,681,585 | 7/1987 | Sayano et al. | 623/6 |
| 4,715,858 | 12/1987 | Lindstrom | 623/5 |

FOREIGN PATENT DOCUMENTS

| | | | |
|---|---|---|---|
| 2556728 | 6/1985 | France . | |
| 2081469 | 2/1982 | United Kingdom | 623/5 |
| 2151244 | 7/1985 | United Kingdom . | |

OTHER PUBLICATIONS

"The Jaffe Single Piece Posterior Chamber Lens from CILCO" Advertisement Brochure from Cilco (2 pp.) 623/6 Oct. 1984.

"Intraoperative Management of the Torn Posterior Capsule" R. H. Osher, 1985 Techniques in Ophthalmic Surgery, vol. 1, No. 5, 65–79.

"Sodium Hyaluronate Vitrectomy" by D. W. Langerman, J. Cataract Refract. Surg., vol. 12, Jan. 1986, pp. 69–72.

*Primary Examiner*—Randall L. Green
*Assistant Examiner*—Mary Beth O. Jones
*Attorney, Agent, or Firm*—Norbert P. Holler

[57] ABSTRACT

For use in ophthalmic surgery, the surgeon has available a supply of "spare parts" which are artificial members, possibly simulating different components of the eye, that are suited, depending on their structural forms and shapes, for surgical implantation in the eye as and/or in connection with repair and/or reinforcement and/or replacement structures for damaged or diseased eye components. The members basically are made of cohesive sheet materials of biocompatible substances such as cross-linked hyaluronic acid, PMMA, or other equivalents thereof. Certain of such "spare parts" are particularly well suited for dealing with the problem of the torn posterior capsule when encountered during an extracapsular cataract extraction.

17 Claims, 7 Drawing Sheets

Fig. 9.
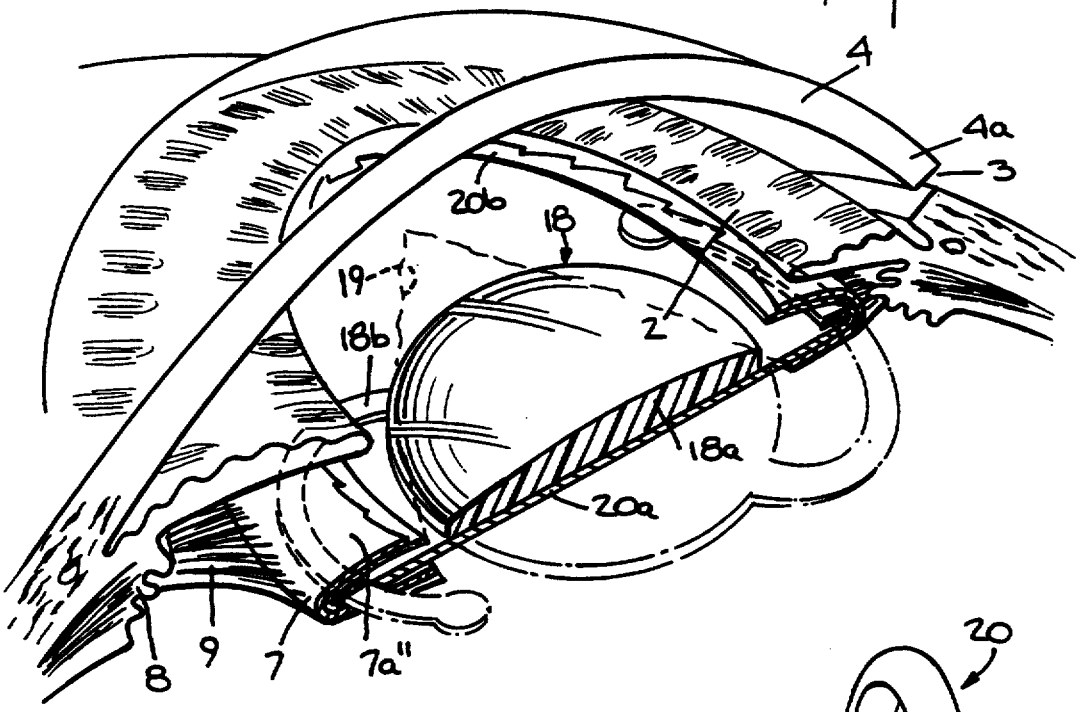
Fig. 10.
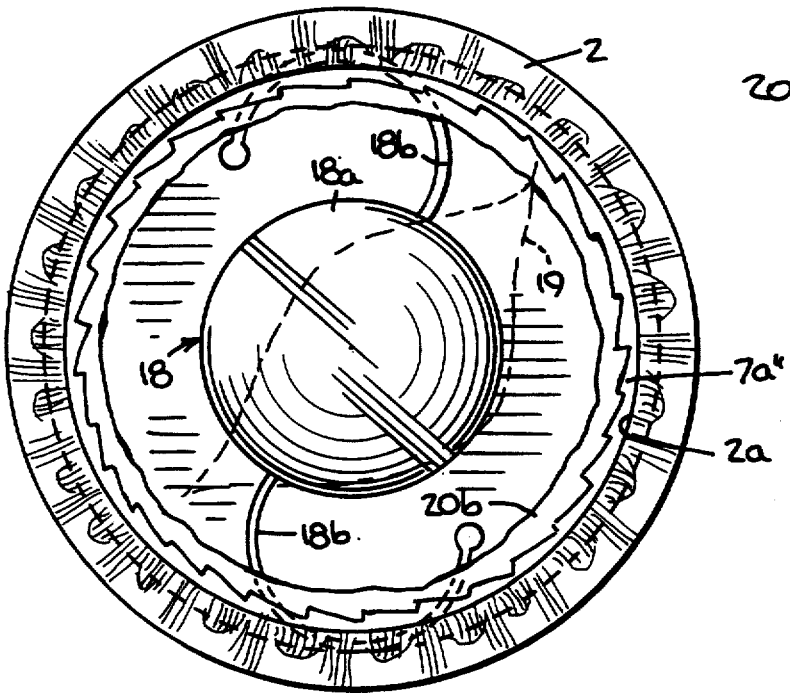
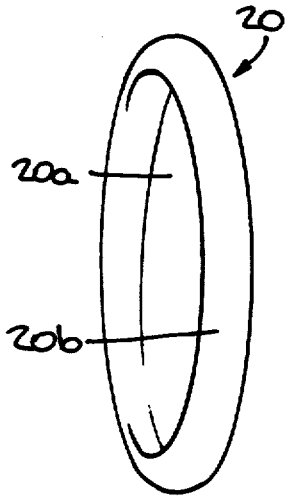
Fig. 7.

Fig. 16.
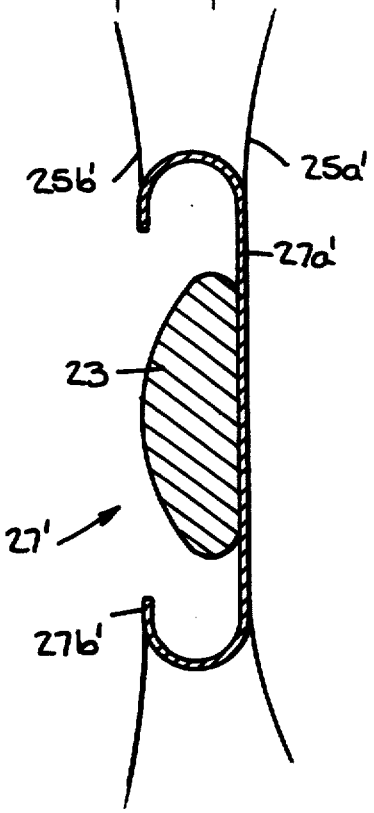
Fig. 16A.
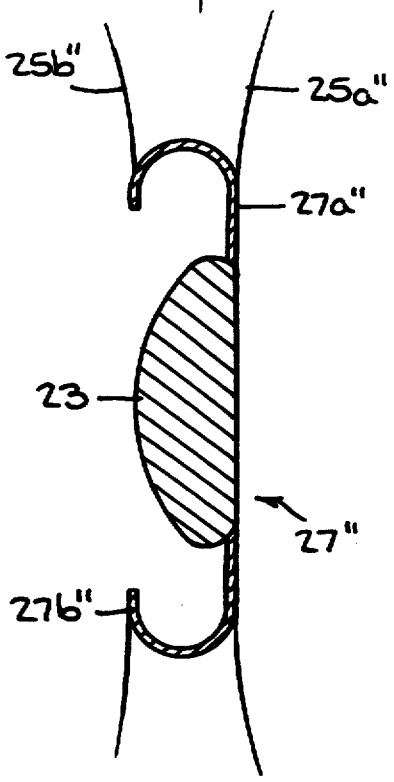
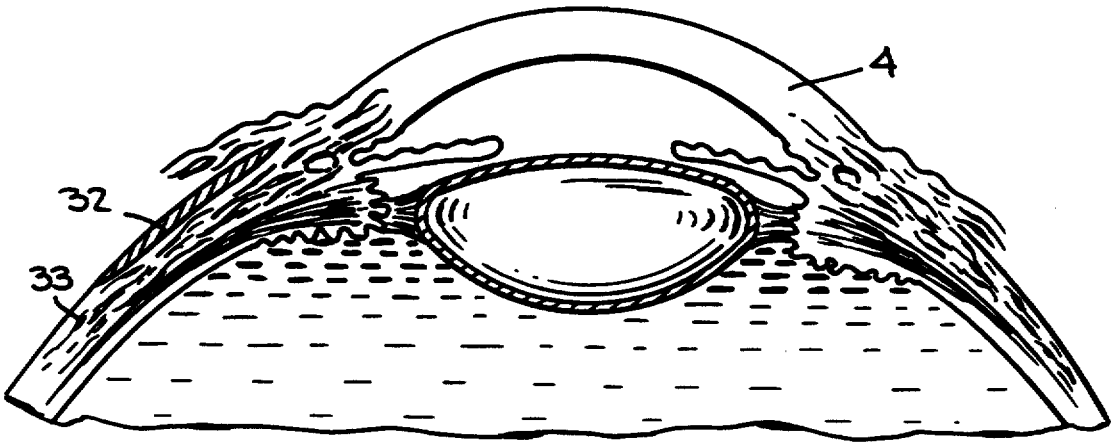
Fig. 22.

Fig. 20.
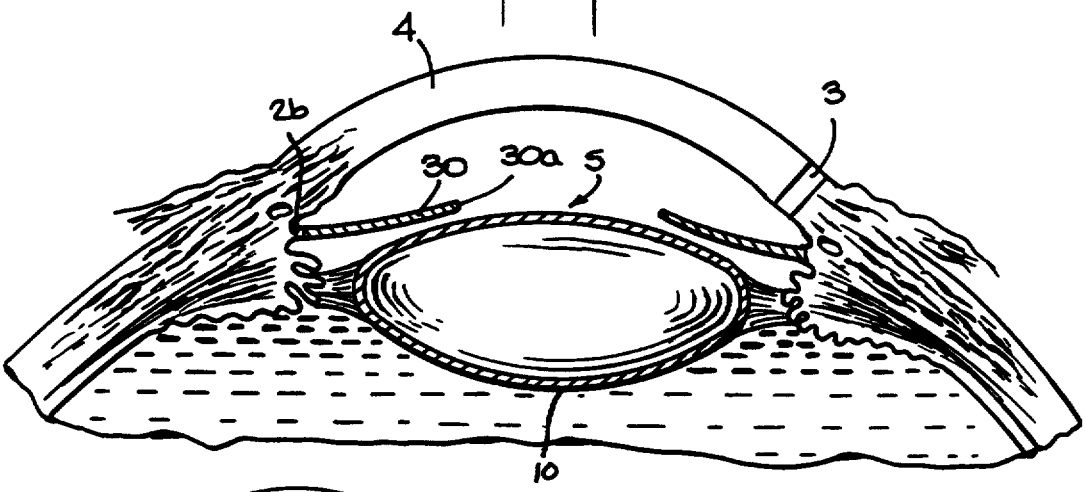
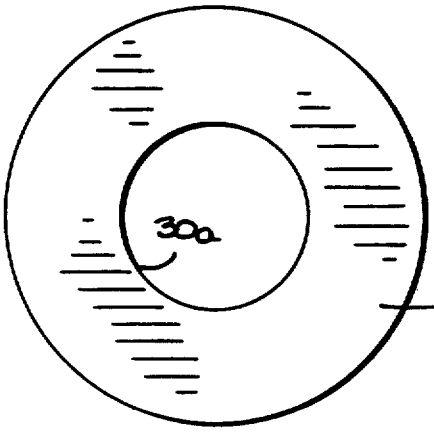
Fig. 19.
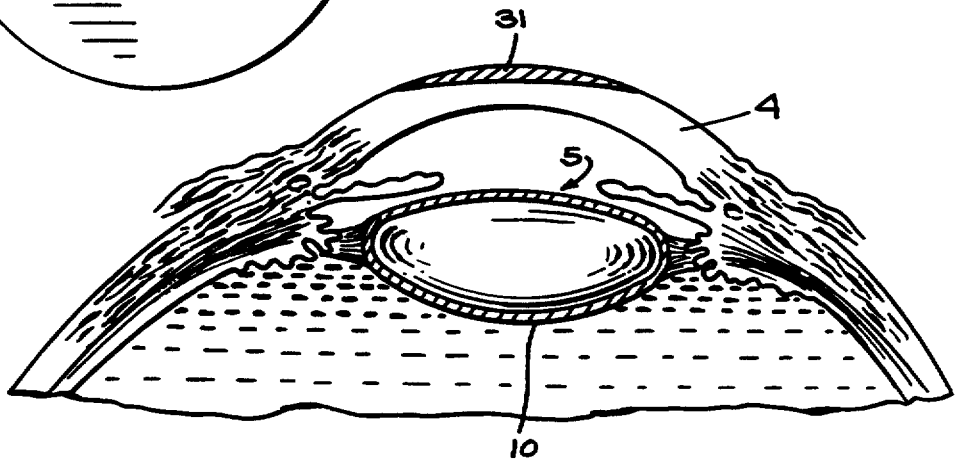
Fig. 21.

"SPARE PARTS" FOR USE IN OPHTHALMIC SURGICAL PROCEDURES

Matter enclosed in heavy brackets [ ] appears in the original patent but forms no part of this reissue specification; matter printed in italics indicates the additions made by reissue.

This invention relates to the art of ophthalmic surgical procedures, and in particular to a class of novel "spare parts" adapted for use by ophthalmic surgeons in the course of such procedures.

As will become apparent from the following description, the applicability of the principles of the present invention is fairly wide and general. For the sake of an orderly presentation, therefore, and to facilitate comprehension of those principles, the description will be focused in the first instance on those surgical procedures which involve the removal of a cataract from a human eye, with other applications being set forth subsequently.

BACKGROUND OF THE INVENTION

Generally speaking, the portion and components of a human eye with which the present invention is most closely concerned, though well known to those skilled in the art, are illustrated and labeled for lexicographic purposes in FIG. 1 of the hereto appended drawings. The eyeball (which is suspended in the orbit by various types of tissues and muscles and is protected in front by the upper and lower eyelids, all not shown) is enclosed in three layers or coats of which only the outer one, the sclera, is explicitly represented (the other layers being the retina and the choroid coat). At the front of the eye, the place of the sclera, which is white and opaque, is taken by the cornea which is transparent and adjoins the sclera at the limbus under the conjunctiva. Located behind the cornea are the iris and the lens, with the lens being suspended in place by the ciliary zonule or zonular fibers which are connected at one end to the lens and at the other end to the ciliary body. The iris, which normally rests against the front of the lens (although for the sake of clarity it is shown in FIG. 1 as being spaced somewhat therefrom) is actually a continuation of the choroid coat starting from a location just anteriorly of the ciliary body and is provided in the middle with a circular opening, the pupil, through which light entering the eye through the cornea is able to reach the lens. The space between the cornea and the iris constitutes the anterior chamber of the eye, with the peripheral region where the cornea and the iris meet constituting the angle of the anterior chamber, and the space between the iris and the lens constitutes the posterior chamber, with these two chambers, which communicate through the pupil, being filled with a watery fluid, the aqueous humor. The space in the eyeball behind the lens is filled with a transparent jelly-like substance, the vitreous humor. The lens itself includes a viscous nucleus of inert material enclosed by layers of fibers which in turn are surrounded by an elastic membrane or capsular bag, with that part of the bag which is located at the side of the lens facing the iris and cornea being designated the anterior capsule, and with that part of the bag which is located at the side of the lens engaging the hyaloid face of the vitreous humor being designated the posterior capsule. The hyaloid face is a skin-like somewhat denser region of the vitreous humor which constitutes the boundary of the latter at its interface with the posterior capsule and the ciliary zonule. The cornea, the aqueous humor, the lens and the vitreous humor constitute the refractive media through which light entering the eye passes prior to reaching the retina, with the cornea constituting the main light-refracting structure while the lens, a relatively minor part of the overall optical system, constitutes principally the means of varying the focus.

It is readily apparent, therefore, that corrective ophthalmic surgery is an aspect of the field of medicine in which eye surgeons are required to perform extremely delicate operations on a highly sensitive body organ which per se is relatively small and in addition is located in a relatively small and not easily accessible space. Moreover, of such operations, which may range from reinforcement to repair to removal and replacement of individual eye components, some necessitate the insertion of one or more surgical tools into the interior of the eye through a very small corneal incision and entail the performance of extensive manipulations of such tools, thereby creating a substantial risk, no matter how talented and careful the surgeon may be, that occasionally some unintended serious and potentially dangerous damage may be done to tissues and components of the eye.

As is well known, human beings, especially elderly persons, tend to develop a degree of opacity or clouding of the lens fibers surrounding the inert nucleus. The condition where this opacity spreads into the center of the lens in the region behind the pupil so as to impair vision, is designated cataract. When the opacity has progressed sufficiently to cause the loss of useful functional vision, the cataract is said to be mature, and the only currently available treatment for that condition is the removal of the cataract by extraction of the lens from the eye. Such a cataract removal, which is probably one of the most common and widely performed ophthalmic surgical procedures these days, may involve either an intracapsular or an extracapsular extraction of the lens.

In an intracapsular extraction, the entire lens, including the nucleus, the cortex (the fibers) and the enveloping capsular bag, is taken out as a unit, with the zonular fibers which connect the bag to the ciliary body being first dissolved and the cataract then being removed with the aid of a low temperature probe. In such a case, the removal procedure is usually followed by the implantation of an intraocular lens (IOL) into the anterior chamber of the eye, with the lateral position fixation elements (resilient loops, arms, or the like) being received in the angle of the anterior chamber defined between the outer periphery or rim of the iris and the back of the cornea in the limbal region thereof, although it has also been proposed to implant the IOL in the posterior chamber, with the position fixation elements being received in the ciliary sulcus, subject to the provision that steps are taken to ensure that the IOL does not fall into the vitreous humor.

In an extracapsular extraction, by way of contrast, first a major portion of the anterior capsule is cut away, leaving in place only that part of the capsular bag which consists of the posterior capsule and the remaining annular anterior capsular flap, then the lens nucleus is extracted from the capsular bag by any well-known type of expression or by phacoemulsification, and finally the cortex is removed by irrigation and aspiration. In such a case, the removal procedure is usually followed by the implantation of an IOL into the posterior chamber of the eye, with the position fixation elements being received either in the ciliary sulcus (with the residual capsular bag isolating the IOL from the vitreous humor) or in the residual capsular bag at the equatorial region thereof where the anterior capsular flap adjoins the posterior capsule.

Either of these cataract extraction procedures may, however, lead to an unfortunate development. Thus, the removal of the entire lens (nucleus plus capsular bag) in an intracapsular extraction may result in a distortion of, and in the resultant creation of a break or tear in, the hyaloid face at the anterior boundary of the vitreous humor. On the other hand, the removal of the lens nucleus out of the capsular bag, whether by expression or by phacoemulsification, in an extracapsular extraction may lead to the posterior capsule being torn, which very likely will lead to the integrity of the hyaloid face being correspondingly impaired as well. As is known from the literature, and as every ophthalmic surgeon knows from experience, there are many ways in which a posterior capsule can be torn during an extracapsular cataract extraction, and no surgeon, no matter how careful, is immune to encountering a torn posterior capsule at some time or other. See, for example, Osher, R. H., "Intraoperative Management of the Torn Posterior Capsule" published in 1985 Techniques in Ophthalmic Surgery, Volume I, No. 5, pages 65–79. Irrespective of whether the removal procedure is intracapsular or extracapsular, of course, the taking of prompt steps to mitigate and counteract the effects of the tear, be it only in the hyaloid face or only in the posterior capsule or in both of them, is absolutely essential in order to prevent any prolapse of the vitreous humor into the anterior chamber, which could lead to traction on the vitreous humor base and a consequent detachment of the retina.

BRIEF DESCRIPTION OF THE INVENTION

It is an object of the present invention, therefore, to provide an ophthalmic surgeon with means extrinsic to the natural eye of a human being (or an animal, for that matter) which are not in the nature of surgical tools and adjuncts thereof but which can be used by the surgeon to promptly and efficaciously seal a tear that may have occurred in the posterior capsule of the eye or in the hyaloid face, or in both of them, during a cataract extraction procedure, thereby to inhibit a potentially deleterious prolapse of the vitreous humor into the anterior chamber of the eye.

A more particular object of the present invention is to provide an ophthalmic surgeon with a supply of suitably shaped and configured structural members of a cohesive biocompatible sheet material each of which can be selectively surgically introduced into an eye after completion of a cataract extraction procedure so as to have at least a portion of such member positioned to overlie and seal a tear in the hyaloid face or the posterior capsule.

It is also an object of the present invention to provide such structural members in forms rendering them capable of use either as a patching element to be inserted into a residual endogenous capsular bag having a torn posterior capsule or as a full replacement for an extracted endogenous capsular bag, in either case with or without a built-in capability of providing optically refractive properties.

A more generalized object of the present invention, then, is to provide a supply of structural members or "spare parts" of a cohesive biocompatible sheet material which are adapted for use by ophthalmic surgeons in a variety of surgical procedures that can be performed on various components of the eye for the purpose of either repairing or strengthening or replacing such components.

Generally speaking, and again focusing in the first instance on cataract surgery, in accordance with the currently contemplated best mode of the present invention the objectives of the invention are attained through the use of a biocompatible cohesive sheet material made of cross-linked pure and non-inflammatory hyaluronic acid or any of the functionally equivalent salts thereof. It should be noted, in this regard, that hyaluronic acid is a natural high viscosity polymer of acetylglucosamine and glucuronic acid which is found, usually in the form of its sodium salt, in various parts of the human body including the vitreous humor (it is also found in various types of animal tissues, e.g., rooster combs), and that this substance in its viscous flowable state has heretofore been proposed for use in connection with cataract extractions and IOL implantations. Thus, viscoelastic sodium hyaluronate, which is available from Pharmacia, Inc. under the registered trademark "Healon", has been promoted, in that company's advertising, for use in connection with the implantation of an IOL into the capsular bag remaining after an extracapsular cataract extraction, with the "Healon" serving as a sort of flushing material to separate the posterior capsule of the lens from the anterior capsular flap so as to facilitate the placement of a posterior chamber lens implant within the capsular bag. The material has also been promoted for use, inter alia, as a viscoelastic pressure medium adapted to be directed at the edge of the pupil so as to serve as a sort of mechanical pupil dilator for the purpose of obtaining an extra 1 or 2 mm of pupillary dilation, as a means for repositioning a prolapsed iris during phacoemulsification, as a sort of soft wedge for loosening and separating the lens nucleus from the cortex in the posterior capsule and for "floating" the nucleus into the anterior chamber and out of the eye, etc. Viscoelastic "Healon" (hyaluronic acid or sodium hyaluronate) injected into the posterior chamber after a cataract extraction and upon discovery of vitreous humor in the posterior capsule or in the anterior chamber has further been shown to be useful as a tamponade for temporarily preventing any further loss of vitreous humor until a vitrectomy has been performed and an IOL has been implanted into the bag. See Langerman, D. W., "Sodium Hyaluronate Vitrectomy" published in J. Cataract Refract. Surg., Vol. 12, January 1986, pages 69–72. However, viscous "Healon", by virtue of its viscous state, is not capable of serving as a means for permanently sealing a tear in the posterior capsule or the hyaloid face.

The underlying discovery of the present invention is the recognition that, in contrast to viscous hyaluronic acid, cohesive sheeting of biocompatible cross-linked hyaluronic acid (this term, it should be kept in mind, also encompasses such equivalent substances as the sodium, potassium, calcium and magnesium salts of the acid), such as is also available from Pharmacia, Inc. in a form substantially like those disclosed in U.K. Pat. No. 2,151,244, can be used to provide the surgeon with a supply of preformed, shape-retaining structural members or "spare parts" adapted to be selectively inserted into the eye, from which a cataract has been removed, for the purpose of reinforcing or repairing or replacing a component of the eye affected in some way by the removal of the cataract. The specific type of such a "spare part" which the surgeon will select for use in any given case will, of course, vary with the type of cataract extraction being performed, the condition of the eye, the size and location of the tear (if any), and the attending surgeon's previous experience with and on-the-spot diagnosis of the situation.

More particularly, in accordance with one embodiment of the present invention, for use in the case of an extracapsular cataract extraction the supply of hyaluronic acid sheet "spare parts" may include at least one member which has the shape and configuration of an imperforate disk or strip which can be surgically introduced into the eye through the existing corneal incision made by the surgeon for the cataract extraction procedure and can be positioned onto the anterior surface of the posterior capsule as a patch so as to overlie and cover a tear in the posterior capsule, with the natural adhesion between the hyaluronic acid sheeting and the capsular tissue ensuring that the patch will self-adhere to the posterior capsule and remain in place thereon. Once in place, the patch seals the tear, prevents it from becoming enlarged, and inhibits any migration of vitreous humor into the posterior chamber pending completion of the IOL implantation procedure (any vitreous humor that may have already entered the posterior chamber through the tear is removed by standard vitrectomy techniques prior to the implantation of the patch and, if at all possible, prior to the escape of the vitreous humor into the anterior chamber). If the subsequently implanted IOL also happens to have a convex posterior surface, of course, that surface will be in engagement with the posterior capsule and the patch thereon and will assist in the retention of the seal at the location of the tear.

In accordance with another embodiment of the present invention, the supply of hyaluronic acid sheet "spare parts" may include at least one member which, also for use in the case of an extracapsular cataract extraction, has been preformed into the shape and configuration of an artificial anteriorly incomplete capsular bag, i.e., a structure having a posterior capsule-like portion and an annular anterior capsular flap-like portion and thus being essentially similar in form to the residual endogenous capsular bag which remains in the eye after an extracapsular extraction procedure. Such an artificial capsular bag can be surgically inserted into the endogenous capsular bag so as to in effect constitute a liner and reinforcement for the same, with the posterior capsule portion of the inserted capsular bag overlying and covering the endogenous posterior capsule and serving, if required, to seal any tear in the latter in the manner of a patch. The interfitted endogenous and artificial capsular bags then also constitute a receptacle for the IOL to be implanted, in which either the position fixation elements of the IOL (in the case of an IOL having such elements) or the peripheral edge region of the IOL (in the case of an IOL such as a disk lens which has no such elements) will be located and confined behind the annular anterior capsular flap portion of the inserted capsular bag.

It is also contemplated by the present invention that the supply of "spare parts" may include at least one member preformed to have the shape and configuration of a section of a full-shape anteriorly incomplete capsular bag. Such a member thus might have the form of a segment-shaped portion of a capsular bag and might be either produced in that form directly from the starting hyaluronic acid sheet material or cut to that form from a previously produced full-shape capsular bag. A "spare part" according to this variant of the invention is adapted to be used, for example, in a case where a region of weakness or a tear in the endogenous capsular bag is located in the equatorial zone of the capsular bag, i.e., in the region thereof where the anterior and posterior capsules are joined to each other, and/or in any case where the surgeon determines that the insertion of a full artificial capsular bag is either not warranted or actually counterindicated, e.g., where the tear is in the peripheral region of the posterior capsule but does not extend to the center thereof.

In accordance with yet another embodiment of the present invention, the supply of "spare parts" may include at least one member which has the basic form of an artificial anteriorly incomplete capsular bag as aforesaid but which is specifically designed to be introduced into the eye after an intracapsular cataract extraction. Such a capsular bag would be modified in its structure only by being provided along the exterior peripheral regions of its posterior capsule portion and its anterior capsular flap portion with a plurality of circumferentially distributed, generally radially extending artificial zonular fibers, also made of hyaluronic acid sheet material, to enable the bag to be connected to the ciliary body. This type of capsular bag, when inserted and mounted in the eye, is adapted to constitute a receptacle and the sole support for the subsequently implanted IOL, with the posterior capsule portion of the inserted capsular bag overlying and bearing directly against the hyaloid face and together with the implanted IOL serving to support the vitreous humor and, if necessary, to seal any break or tear that might have been formed in the hyaloid face.

In accordance with still another embodiment of the present invention, the supply of "spare parts" may include at least one member in the form of either of the two types of artificial anteriorly incomplete capsular bags described above, with such member being modified in its structure to include a built-in optic or lens body supported by the posterior capsule portion of the artificial capsular bag, so that the insertion of the bag automatically causes an IOL to be implanted in the eye and thereby obviates the need for a later separate IOL implantation procedure. To this end, the optic may be made, for example, of a relatively hard material such as polymethylmethacrylate (PMMA), or it may be made of a relatively soft material such as silicone, hydrogel, or the like, with the body of the lens being curved and/or compounded to have light-refractive properties. The lens body preferably is secured to the posterior capsule portion of the bag either by being bonded adhesively to the anterior surface of the posterior capsule portion or by being fused along its periphery to the circumferential boundary edge of an appropriately dimensioned opening or hole cut into the posterior capsule portion.

In accordance with a further embodiment of the invention, the supply of hyaluronic acid sheet "spare parts" may include at least one member preformed to the shape and configuration of a lens-shaped body constituted of a full anteriorly complete capsular bag, i.e., one having both an imperforate anterior capsule portion and an imperforate posterior capsule portion sealed to each other along their peripheries, which is filled with a quantity of a suitable inert and biocompatible substance having light-refractive properties and is provided along the exterior peripheral regions of its anterior and posterior capsule portions with a plurality of circumferentially distributed, generally radially extending artificial zonular fibers also made of hyaluronic acid sheet material, to enable the bag to be connected to the ciliary body. This type of "spare part," when inserted and mounted in the eye, is adapted to constitute an accommodative lens and may be implanted in the patient's eye at any time, even many years after the actual removal of the cataract and irrespective of whether the extraction was intracapsular or extracapsular.

As previously intimated, the present invention also contemplates the provision of "spare parts" which are designed for application to ophthalmic surgical procedures other than cataract extractions and hence are appropriately modified in structure and/or form. The characteristics and manner of use of such "spare parts" as well as other aspects of the present invention will be more fully set forth as the description proceeds. [CL]

BRIEF DESCRIPTION OF THE DRAWINGS

In the drawings, which are basically schematic or diagrammatic in nature and should be viewed as such:

FIG. 7 is a perspective illustration of an artificial anteriorly incomplete capsular bag constituting a "spare part" according to another embodiment of the present invention;

FIG. 9 is a view similar to FIG. 8 and illustrates an IOL implanted in the eye within the receptacle constituted by the interfitted endogenous and artificial capsular bags;

FIG. 10 is a plan view of the interfitted capsular bags and the implanted IOL shown in FIG. 9, with the cornea omitted for the sake of clarity;

FIGS. 16 and 16A are sectional views of the capsular bag of the type shown in FIG. 15 and illustrate the same with optics built in accordance with the illustrations of FIGS. 12 and 12A;

FIG. 19 is a plan view of a "spare part" having the form of an annular disk in accordance with another embodiment of the present invention;

FIG. 20 is a section through an eye similar to FIG. 1 and illustrates the disk of FIG. 19 implanted into the eye as an artificial iris;

FIG. 21 is a section through the eye similar to FIG. 1 and illustrates the use of a disk-shaped or strip-shaped "spare part" according to another embodiment of the present invention as an overlay for a section of the cornea in the region of the optical axis; and FIG. 22 is a section through the eye similar to FIG. 21 and illustrates the application of a similar disk-shaped or strip-shaped "spare part" according to the present invention as a reinforcement for a thinned region of the sclera to one side of the eye.

DETAILED DESCRIPTION OF THE INVENTION

Figure 1:
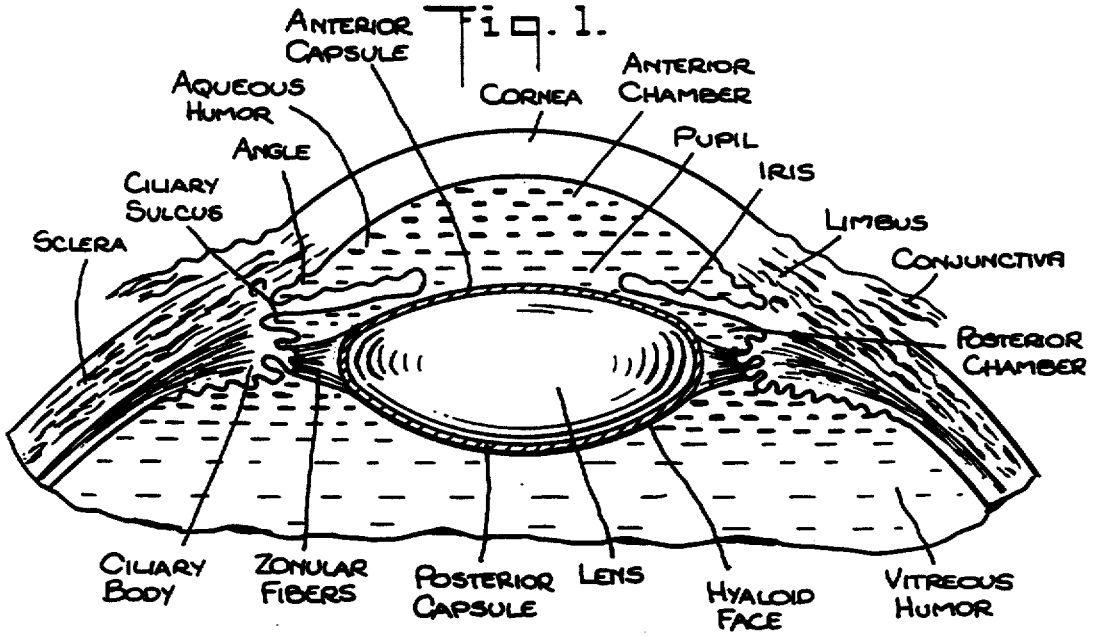
FIG. 1, which has already been discussed previously herein, is an axial section taken through a normal human eye, independent of any particular surgical procedure to be performed thereon, and is intended merely to identify, for purposes of reference, the various components of the eye which are pertinent to an understanding of the present invention.
Figure 2:
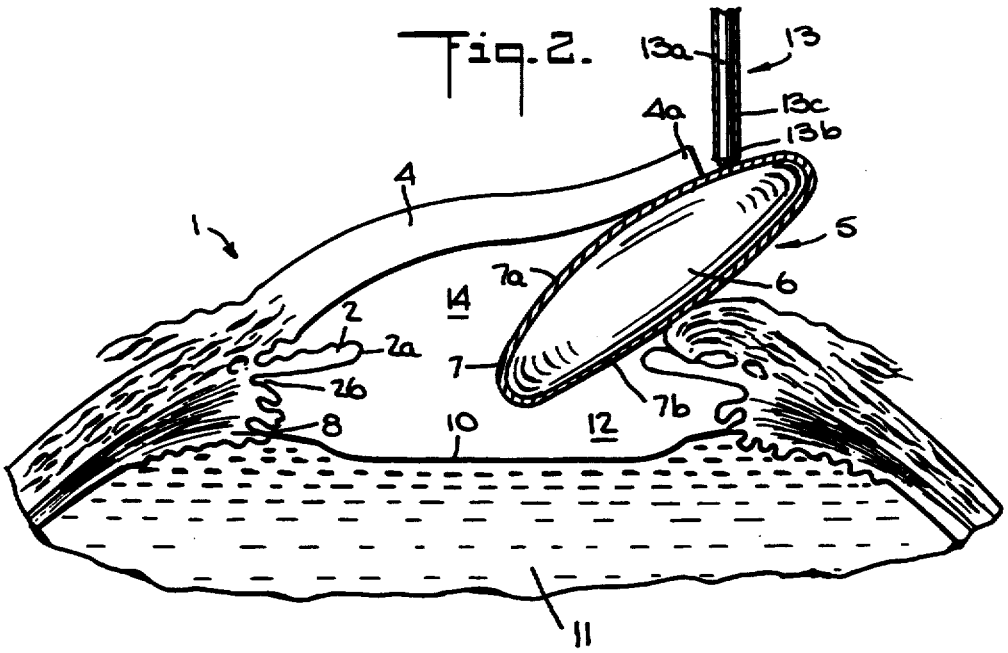
FIG. 2 is a similar section through an eye and illustrates an intracapsular cataract extraction in progress.
Figure 3:
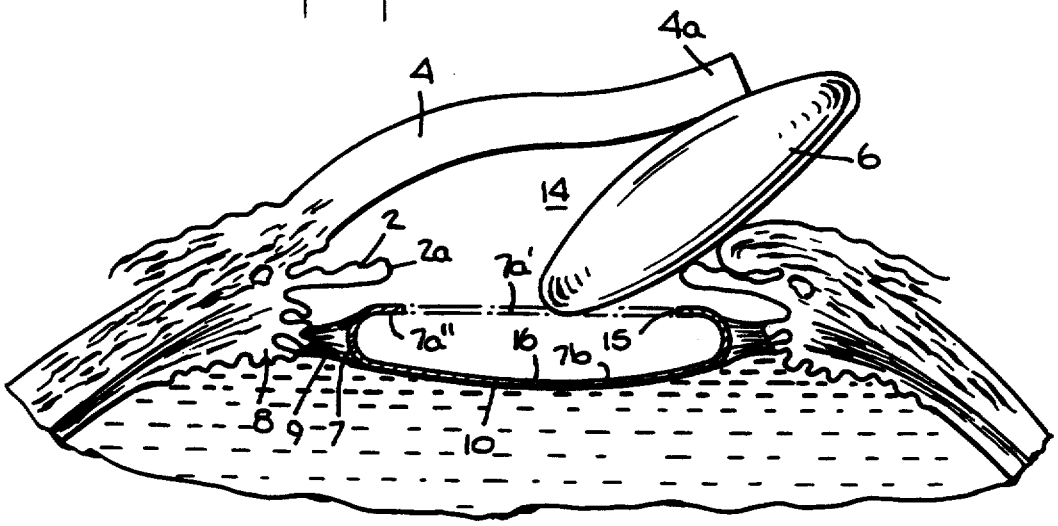
FIG. 3 is a view similar to FIG. 2 and illustrates an extracapsular cataract extraction in progress, also showing the existence of a tear in the residual endogenous posterior capsule.
Figure 5:
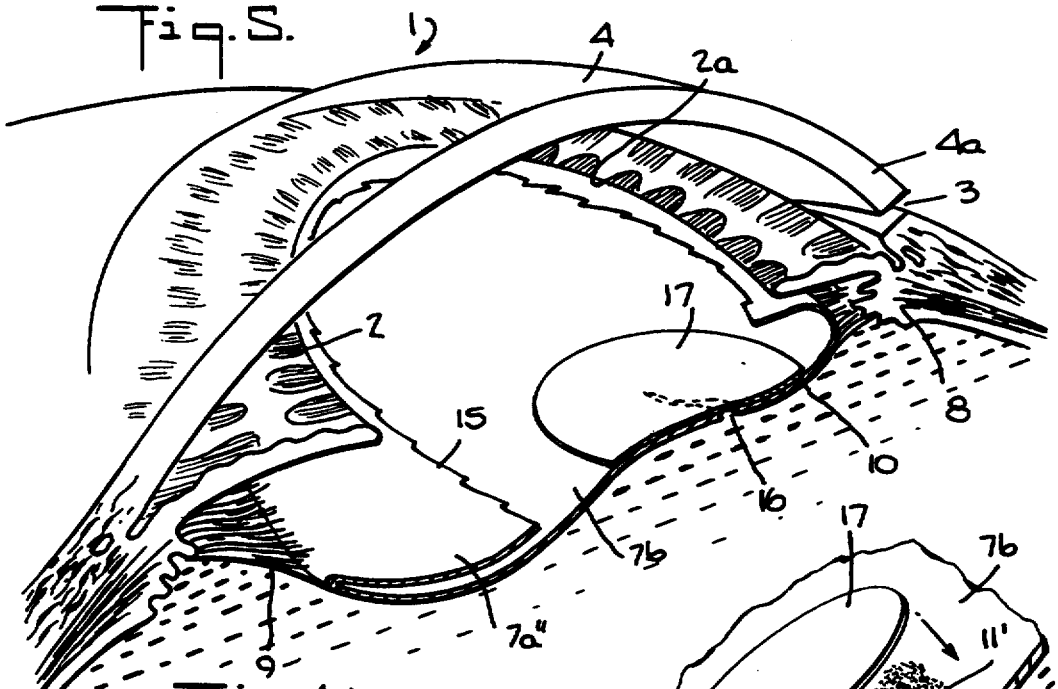
FIG. 5 is a fragmentary, partly sectional, perspective illustration of the eye after completion of the extracapsular cataract extraction and the positioning of the patch of FIG. 4 onto the posterior capsule.

Referring now to the drawings in greater detail, an intracapsular and an extracapsular cataract extraction in progress are shown in FIGS. 2 and 3. As is well known and, consequently, has not been explicitly illustrated, in each of the two operations the eye 1 is first subjected to a conventional preparatory treatment during which the eye is anesthetized with a retrobulbar block and the iris 2 is treated to dilate the pupil 2a, following which an appropriate incision 3 (best visualized in FIGS. 5, 6, 8 and 9) is made in the cornea 4 along one section of the perimeter thereof, i.e., just anteriorly of the limbal region, so that the resultant corneal flap 4a can be lifted sufficiently to provide the surgeon with the requisite degree of access to the interior of the eye. The dilation of the pupil 2a provides the maximum possible exposure of the lens 5 which consists of the nucleus 6, the cortex (not shown) and the enveloping capsular bag 7 therefor constituted by the peripherally joined anterior capsule 7a and posterior capsule 7b. The lens is attached along its entire periphery to the ciliary body 8 by zonular fibers 9, and normally the posterior capsule 7b is in full surface contact with the hyaloid face 10 of the vitreous humor 11, as shown in FIG. 1.

Turning now in particular to FIG. 2, in the case of the intracapsular cataract extraction the surgeon, after the incision has been made, first injects a suitable enzyme, e.g. an alpha-chymotrypsin, into the posterior chamber 12 to dissolve the zonular fibers 9 around the entire periphery or equatorial zone of the endogenous capsular bag 7 and thereby disconnect the lens 5 from the ciliary body. With the corneal flap 4a then appropriately held back, the surgeon inserts the end region of a low-temperature probe 13 (conventionally a thin metal rod 13a covered entirely except for its tip 13b by an insulating sheath 13c) into the eye through the incision 3, the anterior chamber 14 and the pupil 2a to bring the tip of the probe into contact with the anterior capsule 7a of the lens. This causes the portion of the anterior capsule at the contact location and a small region of the lens nucleus under and around the contact location to freeze and thereby to adhere to the tip of the probe, whereupon the lens is loosened from the hyaloid face 10 and is then lifted bodily out of the eye. (Of course, the removal of the cataract in an intracapsular cataract extraction procedure can also be effected by other suitable techniques not necessary to describe in detail herein, for example, any of the various techniques for this purpose which were well known before the "freeze" method was developed.)

In the case of the extracapsular cataract extraction (FIG. 3), on the other hand, after the corneal incision has been made, the zonular fibers 9 are not touched. Rather, a major interior portion [7a,] *7a'* of the anterior capsule 7a, which portion is shown only in phantom outline in FIG. 3 and is the portion located just behind the dilated pupil 2a, is cut away along a generally circular locus 15 (see also FIG. 5) substantially coinciding with (albeit slightly smaller than) the expanse of the dilated pupil. It will be understood, therefore, that after the severed portion 7a' of the anterior capsule has been removed, the endogenous capsular bag 7 is still located in the eye but only in an anteriorly incomplete form, i.e., consisting of the posterior capsule 7b and the residual annular anterior capsular flap 7a''. Thereafter, the lens nucleus 6 is expressed from the residual capsular bag by conventional techniques well known in the art, which may entail the use of a muscle hook and a lens loop (not shown) aided, if deemed appropriate by the surgeon, by an injection of viscous sodium hyaluronate into the residual capsular bag to enable the lens nucleus to be floated out of the bag through the pupil and into the anterior chamber, or which may as an alternative entail the use of phacoemulsification to break up and emulsify the nucleus preparatory to its removal from the eye (in this alternative, of course, the nucleus would not have the cohesive form shown in FIG. 3 but would be amorphous). In either procedure, the removal of the nucleus is followed up by removal of the cortex through irrigation and aspiration.

It should be kept in mind, in regard to the herein set forth descriptions of the two types of cataract extractions, that FIGS. 2 and 3 (and for that matter all the other figures of the drawings) are purely diagrammatic illustrations the purpose of which is to facilitate an understanding of those procedures and of the still to be described principles and embodiments of the present invention. The illustrations are not intended to represent in precise detail the various aspects of the physiological structures and surgical techniques involved in the two operations.

Referring now to FIGS. 3–10, in the case of an extracapsular cataract removal it is imperative that the surgeon should be able to deal expeditiously with probably the most immediate of the various complications to the patient that can result from the operation, namely, the presence of a tear or rent in the posterior capsule which, due to the extreme thinness of the latter, is almost invariably accompanied by a loss of integrity of the underlying hyaloid face as well and, if unattended to, will permit the vitreous humor to prolapse into the anterior chamber of the eye with potentially dire consequences. The size and location of the tear may vary, of course, and correspondingly the manner of treatment which the surgeon will have to implement will vary with the size and location of the tear.

Figure 4A:
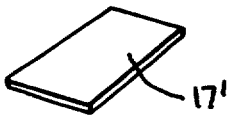
FIG. 4A is a perspective illustration of a strip-shaped patch constituting a "spare part" according to another embodiment of the present invention and suited for use in the same manner as the disk-shaped patch of FIG. 4.
Figure 4:
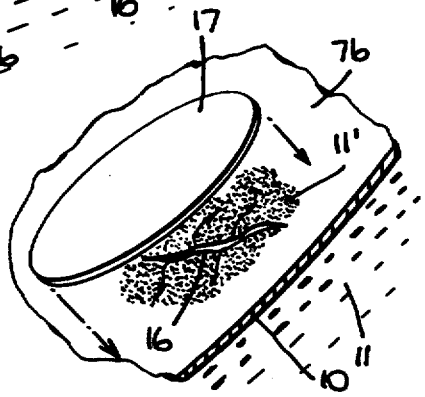
FIG. 4 is a fragmentary, partly sectional, perspective illustration of the posterior capsule in the region of the tear shown in FIG. 3 and further shows, in an exploded view, a disk-shaped patch, constituting a "spare part" according to one embodiment of the present invention, in the process of being deposited onto the posterior capsule over the tear.

Merely by way of example, therefore, in FIGS. 3–6 a tear 16 is illustrated which is relatively small and more or less medially located in the posterior capsule. To deal with such tears, it is contemplated by the present invention that the surgeon will have available a supply of "spare parts" in the form of circular disk-shaped members 17 (FIG. 4) each approximately 5–9 mm in diameter or in the form of rectangular strip-shaped members [17] *17'*, (FIG. 4A) each approximately 5–9 mm long and about 3–5 mm wide and made of a cohesive biocompatible sheet material, for example, cross-linked hyaluronic acid sheeting about 0.03–0.3 mm thick. Thus, upon discovering the tear 16 in the posterior capsule 7b, the surgeon will be able to select a disk 17 or strip 17' and to immediately surgically introduce it into the eye (the member could be folded upon itself, if need be, to facilitate its passage through the corneal incision) and deposit it onto the posterior capsule in overlying relation to the tear (see FIG. 4) so as to serve as a patch therefor. By virtue of the natural affinity of the hyaluronic acid sheet material to the capsular tissue, the member 17 or 17' will self-adhere to the capsule, thereby sealing the tear and preventing any further enlargement thereof as well as any further loss of vitreous humor therethrough. It will be understood that any vitreous humor which may have passed through the tear in the posterior capsule, for example, such as is indicated at 11' in FIG. 4, will be removed by the surgeon through standard vitrectomy techniques immediately prior to the placing of the patch 17 or 17' over the tear.

Figure 6:
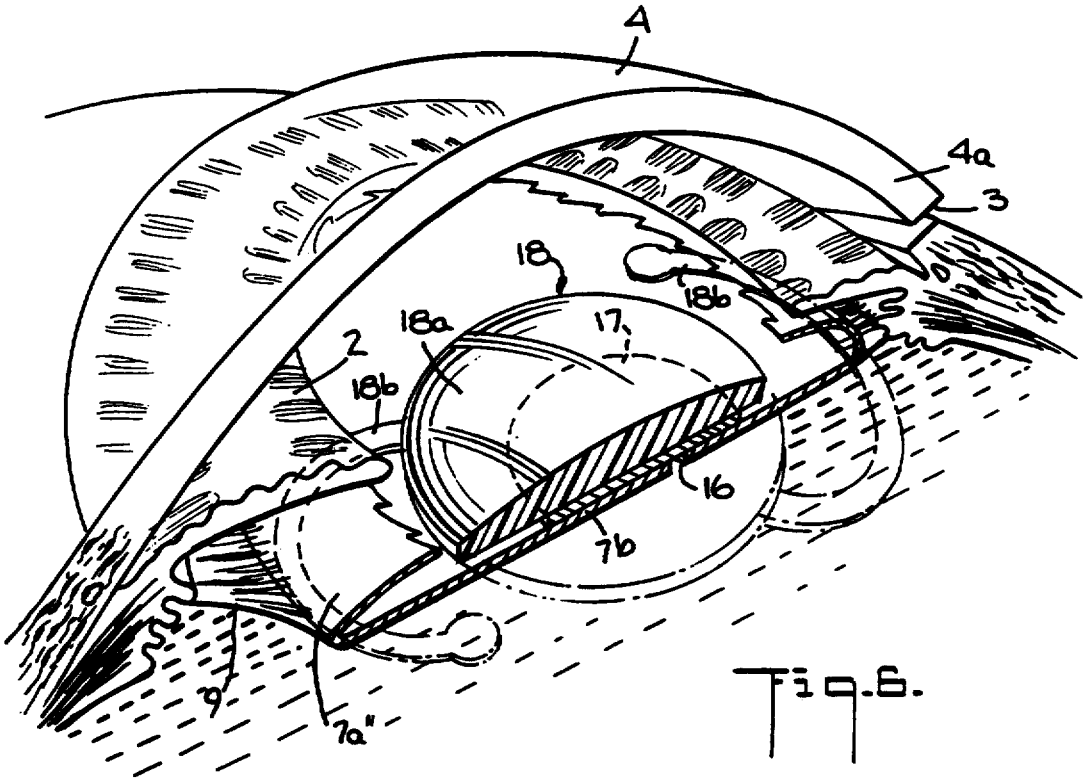
FIG. 6 is a view similar to FIG. 5 and illustrates an IOL inserted into the patched endogenous capsular bag.

Once the patch is in place, the surgeon will be able to proceed, under whatever time schedule is indicated, with the implantation of a posterior chamber IOL 18 (see FIG. 6). It should be pointed out, in this regard, that although the IOL 18 is illustrated in FIG. 6 as having a central optic or lens body 18a and a plurality of lateral flexible position fixation elements 18b, with the latter (which are shown as being open ended arms but could be otherwise configured, e.g. as closed loops) being confined within the peripheral region of the residual capsular bag 7 behind the anterior capsular flap 7a" thereof, the implanted lens could just as well be of a different construction, for example, it could be a disk lens (not shown) having no position fixation elements as such but having a body of sufficiently large diameter to enable its peripheral marginal region to be itself confined within the equatorial zone of the residual capsular bag behind the anterior capsular flap. In either case, therefore, the residual endogenous capsular bag constitutes a receptacle for the IOL which, after its implantation, will assist in maintaining the tear firmly sealed.

Figure 8:
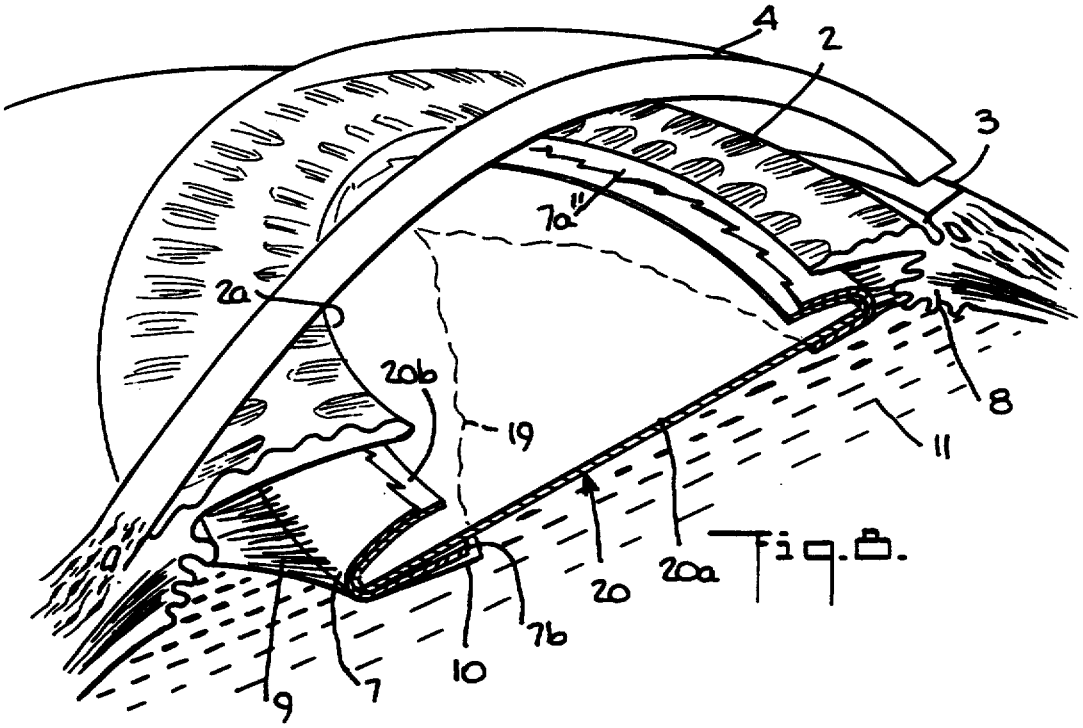
FIG. 8 is a view similar to FIG. 5 and illustrates, as the aftermath of an extracapsular cataract extraction, an endogenous capsular bag with a tear in the posterior capsule extending into the peripheral region or equatorial zone thereof and the patching of the tear by means of an artificial capsular bag of the type shown in FIG. 7 fitted into the endogenous capsular bag.

On the other hand and also merely by way of example, in FIGS. 8–10 a tear 19 is illustrated which, in contrast to the tear 16, is relatively large and at least partially extends into the peripheral region or equatorial zone as well as over the mid-region of the posterior capsule 7b. To deal with such tears, which do not readily admit of being patched by a relatively small disk or strip, it is contemplated by the present invention that the surgeon's supply of "spare parts" will also include a plurality of artificial anteriorly incomplete capsular bags 20 (see FIG. 7) each made of a cohesive biocompatible sheet material such as crosslinked hyaluronic acid and including a generally circular imperforate posterior wall defining a posterior capsule portion 20a and a generally circular, centrally apertured, anterior wall joined peripherally to the posterior wall and defining an annular anterior capsular flap portion 20b. In form, therefore, the anteriorly incomplete artificial capsular bag 20 essentially duplicates the endogenous capsular bag 7 after the anterior capsule section 7a' of the latter has been cut away.

Thus, upon discovering the tear 19 in the posterior capsule 7b, the surgeon will be able to select an artificial capsular bag 20 from the supply of "spare parts", and to immediately surgically introduce it into the eye (as in the case of the disk 17 or strip [17,,] *17*, the bag 20 could be folded upon itself, if need be, to facilitate its passage through the corneal incision) and implant it into the endogenous capsular bag, with the posterior capsule portion 20a of the artificial artificial *bag overlying the* posterior capsule 7b of the endogenous bag and with the anterior capsular flap portion 20b of the artificial bag underlying the anterior capsular flap 7a" of the endogenous bag. The posterior capsule portion of the artificial capsular bag will then serve as a patch for the torn endogenous posterior capsule (see FIG. 8). The interfitted artificial and endogenous capsular bags furthermore will jointly constitute a receptacle for an IOL (the latter is illustrated in FIGS. 9 and 10 as being the same as the IOL 18 shown in FIG. 6 but could be of a different construction as previously described [herein] *herein*), with the posterior capsule portion 20b of the [herein), with the poster] artificial capsular bag being in full surface contact with the underlying torn endogenous posterior capsule.

It may happen, of course, that a tear will be found either in the equatorial zone of the endogenous capsular bag, i.e., in the region of the juncture between the anterior and posterior capsules, or in a region of the posterior capsule close to the periphery thereof but without the tear being large enough to reach the center or mid-region of the posterior capsule. In such a case, the use of a disk or strip to seal the tear may be found to be either not feasible or not practical. The surgeon may then well decide that the insertion of a full-shape artificial capsular bag 20 into the endogenous capsular bag 7 is neither necessary nor warranted.

Figure 14:
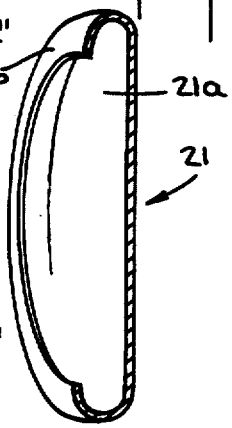
FIG. 14 is a perspective view, similar to FIG. 7, of a segment-shaped portion of an artificial anteriorly incomplete capsular bag constituting a "spare part" according to another embodiment of the present invention.

To deal with such tears, therefore, it is contemplated by the present invention that the surgeon will also have available in the supply of "spare parts" a plurality of members in the form of parts or sections of the full-shape anteriorly incomplete artificial capsular bags. Merely by way of example, a half-circular segment-shaped section 21 of such a bag is illustrated in FIG. 14 and has a posterior wall of generally semi-circular segment shape defining a segment-like posterior capsule portion 21a and an anterior wall of half-circular ring shape having its outer circularly curved periphery joined to the circularly curved periphery of the posterior wall and defining a half-annular anterior capsular flap portion 21b. Such a section of an artificial capsular bag could be formed per se by an appropriate molding technique or it could be produced by appropriately cutting a full-shape artificial capsular bag such as that shown in FIG. 7 in half, i.e., along a diameter, to provide the desired segmental section. If a somewhat smaller bag section were desired, of course, the cut would be made along a chord rather than along the diameter of the circle. In use, the surgeon will implant the bag section 21 into the endogenous capsular bag only at the location of the tear, so that the posterior capsule portion 21a of the artificial capsular bag section overlies and serves as a patch for the region of the endogenous capsular bag where the tear is located and also provides the degree of reinforcement of the bag that is necessary to enable the bag to function acceptably as a receptacle for the subsequently to be implanted IOL.

As previously pointed out, the implantation of an IOL, and in particular a posterior chamber IOL, has currently become an almost automatic concomitant of cataract surgery. While this is conventionally done using an IOL of the form illustrated in FIGS. 6 and 9 (or of a comparable form as herein described), it is contemplated by the present invention that the surgeon's supply of "spare parts" will also include a plurality of artificial capsular bags 22 (see FIG. 11) which in essence are duplicates of the artificial capsular bag 20 shown in FIG. 7, having a posterior capsule portion 22a and an annular anterior capsular flap portion 22b, but are modified to have incorporated therein a built-in optic or lens 23. The built-in intraocular lens 23 may be made of cross-linked hyaluronic acid having an appropriate thickness and curvature and/or being modified through the presence of an appropriate additive so as to have the desired light-refractive properties. Alternatively, the optic 23 can be made of an equivalent material such as polymethylmethacrylate (PMMA), silicone, polysulfone, hydrogel, or like biocompatible substance. As shown in FIG. 12, in which the artificial capsular bag is designated 22', the optic 23 could be bonded directly to the anterior surface of the imperforate posterior capsule portion 22a' of the artificial capsular bag, or, as shown in FIG. 12A, in which the artificial capsular bag is designated 22", the optic 23 may be positioned within the confines of a hole or opening 22c" formed in the posterior capsule portion 22a", with the periphery of the optic being fused to the boundary edge of the hole 22c.

Figure 13:
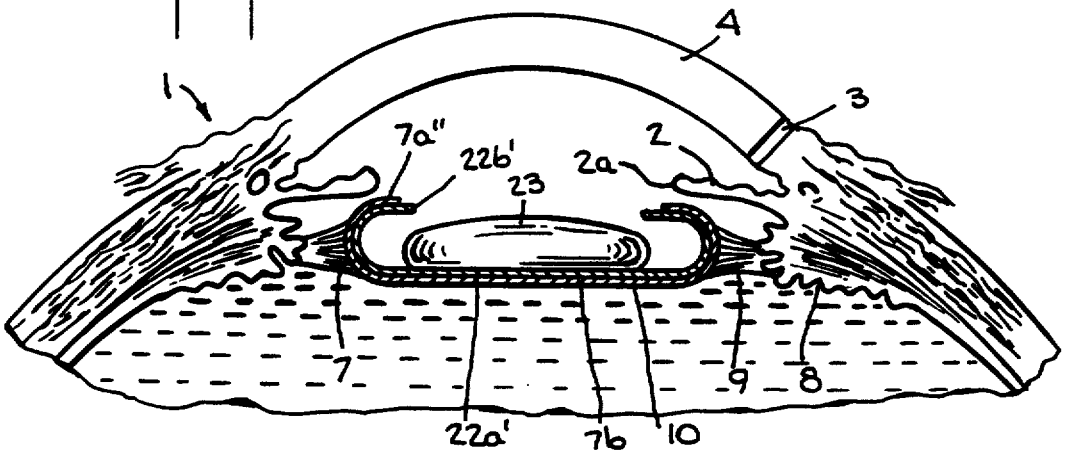
FIG. 13 is a section through the eye similar to FIG. 1 and illustrates the implantation of an artificial capsular bag and built-in optic according to FIG. 11 into the eye following an extracapsular cataract extraction.

Thus, as shown in FIG. 13, the implantation of an artificial capsular bag with a built-in optic into the endogenous capsular bag 7 remaining in the eye following an extracapsular cataract extraction automatically achieves the implantation of a posterior chamber IOL into the eye. For the purposes of this illustration, the artificial capsular bag 22' has been shown as being implanted in the endogenous capsular bag 7, with the posterior capsule portion 22a' overlying the endogenous posterior capsule 7b and with the anterior capsular flap portion 22b underlying the endogenous anterior capsular flap 7a". It will be understood, however, that the implant may just as well be the artificial capsular bag 22".

Merely in passing it might be noted that the implantation of an artificial capsular bag 22' or 22" containing a built-in optic 23 can be utilized in conjunction with an extracapsular cataract extraction that has resulted in a torn posterior capsule, as has been discussed hereinbefore. In FIG. 13, nevertheless, the posterior capsule 7b has been illustrated without a tear therein to indicate to those skilled in the art that the implantation of the artificial capsular bag 22' or 22" may be utilized as a means of implanting an IOL into the eye under that circumstance as well, e.g., in the case of a patient whose cataract was removed a long time, perhaps many years, prior to the implantation but was [ever] *never* replaced by an IOL implant at the time of the removal. It will further be understood that in lieu of implanting an artificial capsular bag with a built-in optic or IOL 23, the surgeon may achieve the same result by utilizing an artificial capsular bag 20 such as is shown in FIG. 7 and inserting thereinto a standard IOL, for example, one such as is designated 18 in FIGS. 6 and 9 (or an equivalent version thereof). Such a capsular bag with an "in the bag" posterior chamber IOL pre-inserted thereinto (not shown) can then be implanted in the patient's eye as a unit in the manner illustrated in FIG. 13.

The various types of "spare parts" described hereinabove and illustrated in FIGS. 4–14 are all designed for use in conjunction with an extracapsular cataract extraction where the endogenous posterior capsule and its adjoining anterior capsular flap remain in the eye to provide an anchoring location for the subsequently implanted "spare parts". In the case of an intracapsular cataract extraction, however, the endogenous posterior capsule is removed from the patient's eye together with the cataract, and thus the aforesaid "spare parts" are initially not adapted for use in conjunction with intracapsular cataract extractions. It is within the contemplation of the present invention, therefore, that the structural characteristics of such "spare parts" which are intended for use in conjunction with intracapsular cataract extractions may be modified somewhat (see FIGS. 15–18) in order to provide means by which they can, after being introduced into the eye, be securely anchored in place.

Figure 15:
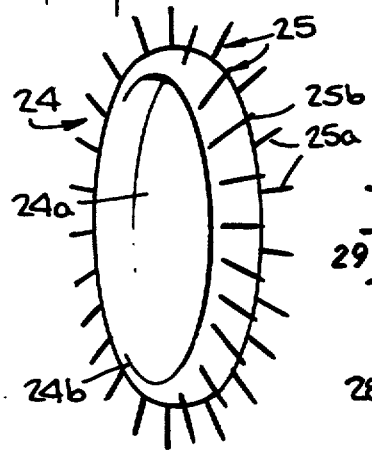
FIG. 15 is a perspective illustration of an artificial anteriorly incomplete capsular bag, either such as that shown in FIG. 7 without a built-in optic or such as that shown in FIG. 11 with a built-in optic, which constitutes a "spare part" according to another embodiment of the present invention" and illustrates the presence of artificial zonular fibers attached to the exterior peripheral regions of the posterior capsule portion and the anterior capsular flap portion of the bag.

Basically, the mentioned structural modification consists of the provision on the respective basic "spare parts" of a plurality of additional "spare parts" in the form of fiber-shaped members which are peripherally distributed about the basic "spare parts" and constitute respective sets of artificial zonular fibers therefor. Thus, as can be seen in FIG. 15, the artificial anteriorly incomplete capsular bag 24 there shown, which has a posterior capsule portion 24a and an annular anterior capsular flap portion 24b, is essentially identical with the artificial capsular bag 20 shown in FIG. 7 except for the fact that a plurality of artificial zonular fibers 25 are affixed, e.g., by being fused or otherwise bonded along one end region thereof, to the exterior surfaces of the posterior capsule portion 24a and the anterior capsular flap portion 24b. As shown, those of the artificial zonular fibers which are designated 25a are distributed over the entire peripheral region of the posterior capsule portion 24a, while those of the artificial zonular fibers which are designated 25b are distributed along the entire peripheral region of the anterior capsular flap portion 24b. Furthermore, the two sets of artificial zonular fibers 25a and 25b are shown as being staggered with respect to each other, i.e., arranged in an alternating sequence, but it will be understood that this is not an essential feature of the arrangement. The artificial zonular fibers 25 are preferably made of the same material as the artificial capsular bag itself, i.e., also of cross-linked hyaluronic acid. In use, when an artificial capsular bag 24 is being implanted in the eye to replace the removed lens capsule 7 (see FIG. 2), the surgeon will effect the anchoring of the bag in place by attaching the free end regions of the zonular fibers 25 to the ciliary body 8 with the aid of a suitable physiological glue. It will be understood, in this regard, that some of the artificial zonular fibers, especially the fibers 25a, may be attached to the ciliary body in the region of the ciliary sulcus 26.

Figure 11:
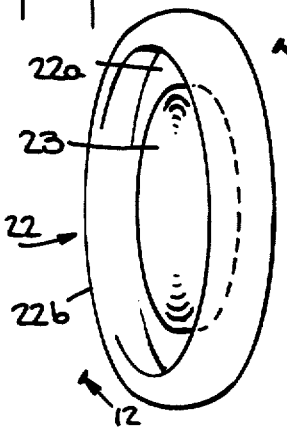
FIG. 11 is a perspective illustration of an artificial anteriorly incomplete capsular bag having an optic or lens body built thereinto and constituting a "spare part" in accordance with another embodiment of the present invention.
Figure 12:
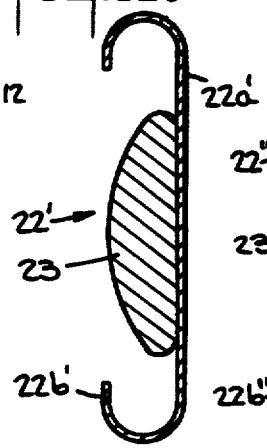
FIG. 12 is a sectional view taken along the line 12—12 in FIG. 11 and illustrates one manner of securing the built-in optic to the posterior capsule portion of the artificial capsular bag.
Figure 12A:
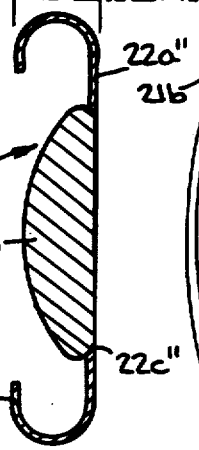
FIG. 12A is a similar sectional view but illustrates another manner of securing the built-in-optic to the posterior capsule portion of the artificial capsular bag.

It will further be understood that the same principle can be applied to the type of artificial capsular bag 22 which is shown in FIG. 11, i.e., to a bag which includes a built-in optic or IOL 23 and which embodies either of the physical forms represented in FIGS. 12 and 12A. Thus, the surgeon's supply of "spare parts" would include at least one artificial capsular bag such as is shown in FIG. 16 and is there designated 27', on which the respective sets of artificial zonular fibers 25a' and 25b' are attached to the outwardly directed surfaces of the imperforate posterior capsule portion 27a' and the annular anterior capsular flap portion 27b', or at least one artificial capsular bag such as is shown in FIG. 16A and is there designated 27", on which the respective sets of artificial zonular fibers 25a" and 25b" are attached to the exterior surfaces of the apertured posterior capsule portion 27a" and the annular anterior capsular flap portion 27b".

Correspondingly, the principle can also be applied to implanting into the eye and securing in place an accommodative lens 28 (FIGS. 17 and 18) which constitutes another "spare part" in the surgeon's supply and has the form of a total, i.e., anteriorly and posteriorly complete, artificial capsular bag 29 having an imperforate posterior capsule portion 29a and an imperforate anterior capsule portion 29b peripherally joined to each other, with the capsular bag being made of cross-linked hyaluronic acid sheet material and being filled with a biocompatible pliable synthetic polymeric material 29c suitably compounded to have light-refractive properties. The anchoring means for the accommodative lens 28 are two sets of artificial zonular fibers 25a''' and 25b''' which are bonded or fused at their inner end regions to the exterior surfaces of the peripheral regions of the posterior and anterior capsule portions 29a and 29b.

Figure 17:
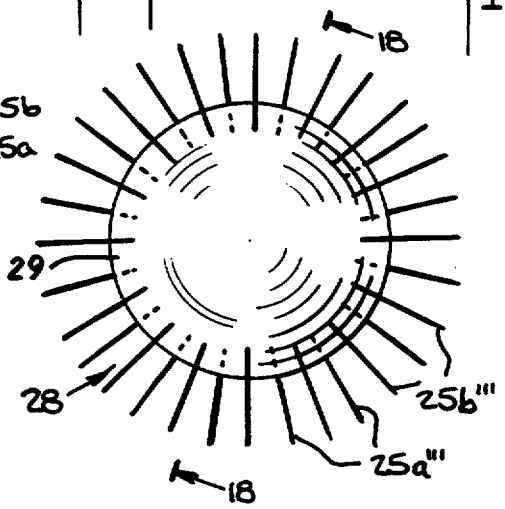
FIG. 17 is a plan view of an artificial complete capsular bag filled with a light-refracting substance and provided with exterior zonular fibers attached to its anterior and posterior capsule portions, which bag constitutes a "spare part" in accordance with another embodiment of the present invention and is designed for use as an accommodative lens.
Figure 18:
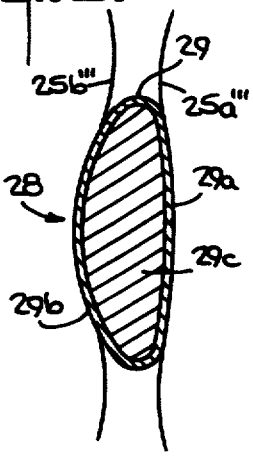
FIG. 18 is a sectional view taken along the line 18—18 in FIG. 17.

Here too, as can be seen from FIG. 17, the two sets of artificial zonular fibers are staggered with respect to each other, but as before this is not an essential feature of the arrangement.

Obviously, when a capsular bag 27′ or 27″ or an accommodative lens 28 is being implanted in the eye, the outer end regions of the associated artificial zonular fibers are attached, with the aid of a suitable physiological glue, to the ciliary body 8. In the case of the lens 28, of course, the attachment of the zonular fibers 25a‴ and 25b‴ to the ciliary body ensures that ultimately the natural contraction and relaxation of the ciliary muscles will effect the desired shortening and lengthening of the focal length of the lens.

The underlying concept of the present invention, namely, the provision of a supply of "spare parts" to be used by an ophthalmic surgeon, is also applicable to the performance of surgical procedures on the eye other than cataract removals. Thus, for use in a case where the iris 2 has been partially or totally removed and the surgeon decides that an implantation of an artificial iris as a replacement for the endogenous iris is indicated, it is contemplated by the present invention that the supply of "spare parts" will include a plurality of annular disks 30 (see FIG. 19) each having a central opening 30a therein and being adapted to simulate an iris. To this end, the outer diameter of each such disk would be sufficient to enable the outer edge of the disk to be appropriately secured, i.e., fused, bonded or sutured, to the residual edge 2b (see FIG. 20) of the excised endogenous iris, while the inner diameter of the disk, i.e., the diameter of the opening 30a, would be approximately equal to the average size of the pupil required for ordinary vision (although in this regard it will be understood that the final determination of a specific diameter of the pupil-simulating opening 30a to be used in any given case will always be made by the physician based on an analysis of the situation and after consultation with the patient).

Likewise, for use in a case where the surgeon decides that a treatment of the cornea, whether for purposes of reinforcement or for purposes of optical property modification, is indicated, it is contemplated by the present invention that the supply of "spare parts" will include a plurality of suitably configured disks or strips 31 (see FIG. 21) of cross-linked hyaluronic acid sheet material each adapted to be attached to the cornea. Merely by way of example, the disk or strip 31 is shown in FIG. 21 as having a thickness that decreases gradually from the mid-region of the disk or strip to its peripheral edge, but it will be understood that its thickness could be substantially uniform throughout (except at the edge) as well and that its curvature could be the reverse of that shown. It will further be understood that the disk or strip 31, having the required shape and curvature, may be applied permanently to the cornea, preferably by suturing, either on the surface thereof (in a procedure analogous to keratomileusis or keratophakia or epikeratophakia) or under its surface (in a procedure analogous to corneal inlay) in the region of the optical axis of the eye where a modification of the refractive properties of the cornea is concerned, or the disk or strip may be applied temporarily to the cornea in a region of thinning thereof (for example, if the stroma has been destroyed down to Descemet's membrane) to serve as a temporary reinforcement of the cornea pending the performance of a conventional corneal transplant operation.

Correspondingly, a disk or strip 32 (see FIG. 22), also having a configuration (shape, size, thickness) appropriate to the circumstances, e.g., the nature of the wound (if any), may be included in the surgeon's supply of "spare parts" for use in connection with components of the eye not involving optical properties. Again merely by way of example, such a disk or strip is shown in FIG. 22 as having been implanted on the sclera 33 just posteriorly of the limbal region thereof where a degree of thinning of the sclera sufficient to reduce its strength (resistance to the internal pressure of the eye) has occurred. Here the disk or strip 32 is shown as having a substantially uniform thickness over its entire expanse except in the edge regions (although it could just as well have a varying thickness as in the case of the disk or strip 31), since the illustrated configuration is not intended to represent the achievement of any degree of optical property modification but rather is intended only to represent that the disk or strip will fill out the region of reduced thickness of the sclera and thereby will reinforce the same so as to compensate for the reduction in strength of the sclera that resulted from the thinning thereof. It will also be understood that a disk or strip of the type shown in FIG. 22 could be used as a "spare part" in still other surgical procedures, for example, as a scleral buckle in retinal detachment procedures.

It should be noted at this point that the emphasis in the preceding description on the "spare parts" being made of cross-linked hyaluronic acid (which, of course, means also the hyaluronates of sodium, potassium, calcium, magnesium, and the like) has been intended for purposes of illustration only and should not be interpreted as precluding the use of other equivalent biocompatible cross-linked or polymer substances. Thus, it is contemplated that the "spare parts" according to the present invention which are to be used by ophthalmic surgeons in the course of ophthalmic surgical procedures may also be made of, for example, such other biocompatible substances as silicone, hydrogel, fibronectin, polymethylmethacrylate (PMMA), polysulfone, combinations of condroitan sulfate and hyaluronic acid, and the like. Also, the term "spare parts" has been used herein to denote only those biocompatible artificial or synthetic members which, whether simulating specific components of the eye or not, are suited, depending on their structural forms and shapes, for surgical use and/or implantation in the eye as repair and/or reinforcement and/or replacement structures or adjuncts for damaged or diseased eye components; the term is not intended to encompass within its meaning or scope such items as the surgical tools and the ancillary materials which a surgeon conventionally uses in the performance of the different surgical procedures during which the "spare parts" of the present invention are adapted to be utilized.

Still further, the mention herein of the surgeon having available a supply of "spare parts" and of the supply in each case including a plurality of the various types of structural members described should not be construed only in the literal and restrictive senses of the words "availability" and "plurality" and "supply". Rather, the concept of "supply available to the surgeon" should be construed broadly; thus, it could mean that the surgeon actually has on hand, irrespective of an immediate need therefor, either a ready supply of one or more of each kind of the various preformed members (disks, strips, capsular bags with or without built-in optics, etc.) or only a quantity of the starting sheet material from which any given desired member can be cut (by a trephine or the like) and/or formed (by a mold or the like) to the required shape and configuration by the surgeon (or an associated technician) as needed preparatory to its being used in a surgical procedure, or it could mean that in anticipation of an upcoming need for any such member the surgeon can obtain the same at that time piecemeal from a manufacturer or other commercial source thereof.

In summary, therefore, it will be seen that in its broadest sense the present invention provides, for use by a surgeon in connection with an ophthalmic surgical procedure, a "spare part" adapted to be surgically introduced into an eye for repair or reinforcement or replacement of a component of the eye, with such "spare part" comprising a member made of a cohesive sheet material of a cross-linked biocompatible substance, and with such member further being preformed into a shape and configuration adapted to the manner in which the involved eye component is to be repaired or reinforced or replaced thereby. Moreover, although various embodiments of structures within the ambit of this invention have been disclosed herein by way of illustration, it is not intended to so limit the invention, since other structures (e.g., sleeves in lieu of disks and strips in appropriate cases, structures which are not merely circular or rectangular but which are differently configured even to the point of being not geometrically regular in shape, etc.) which are equivalent to the disclosed embodiments and which do not entail any departure from the spirit and scope of the present invention as defined in the hereto appended claims, will readily suggest themselves to those skilled in the art.

I claim:

1. For use in connection with ophthalmic surgical procedures; a "spare part" adapted to be surgically introduced into an eye for the purpose of repair or reinforcement or replacement of a component of the eye, said "spare part" comprising a member of a cohesive sheet material of a cross-linked biocompatible substance, said member being preformed into the shape of an anteriorly incomplete capsular bag-like structure which includes a peripherally curved posterior wall defining a posterior capsule portion and a curved strip-like anterior wall defining an anterior capsular flap portion, with said anterior capsular flap portion and said posterior capsule portion being connected to each other along their respective curved outer peripheries, and with said anteriorly incomplete capsular bag-like structure having predetermined physical or optical properties, or both, and being adapted to the manner in which the endogenous posterior capsule of the eye is to be repaired or reinforced or replaced following an intracapsular or extracapsular cataract extraction.

2. A "spare part" according to claim 1, wherein said cross-linked biocompatible substance comprises hyaluronic acid or sodium hyaluronate.

3. A "spare part" according to claim 1, wherein said cross-linked biocompatible substance comprises hydrogel.

4. A "spare part" according to claim 1, wherein said cross-linked biocompatible substance comprises silicone.

5. A "spare part" according to claim 1, wherein said cross-linked biocompatible substance comprises polymethylmethacrylate.

6. A "spare part" according to claim 1, wherein said cross-linked biocompatible substance comprises polysulfone.

7. A "spare part" according to claim 1, wherein said cross-linked biocompatible substance comprises a combination of condroitan sulfate and hyaluronic acid.

8. A "spare part" according to claim 1, wherein said cross-linked biocompatible substance comprises fibronectin.

9. For use in connection with ophthalmic surgical procedures; a "spare part" adapted to be surgically introduced into an eye for the purpose of repair or reinforcement or replacement of a component of the eye, said "spare part" comprising a member made of a cohesive sheet material of a cross-linked biocompatible substance, said member being preformed to have the shape of an anteriorly incomplete capsular bag which includes a generally circular posterior wall defining a posterior capsule portion and a generally circular substantially centrally apertured anterior wall defining an annular anterior capsular flap portion, with said anterior capsular flap portion and said posterior capsule portion being connected to each other along their respective outer peripheries, and with said anteriorly incomplete capsular bag having predetermined physical or optical properties, or both, said member thereby being adapted, when implanted into the part of the endogenous capsular bag of the eye that remains following an extracapsular cataract extraction, to constitute a patch for covering and sealing a tear or rent in the endogenous posterior capsule and to provide a receptacle for an intraocular lens.

10. For use in connection with ophthalmic surgical procedures; a "spare part" adapted to be surgically introduced into an eye for the purpose of repair or reinforcement or replacement of a component of the eye, said "spare part" comprising a member of a cohesive sheet material of a cross-linked biocompatible substance, said member being preformed to have the shape of an anteriorly incomplete capsular bag which includes a generally circular posterior wall defining a posterior capsule portion and a generally circular substantially centrally apertured anterior wall defining an annular anterior capsular flap portion, with said anterior capsular flap portion and said posterior capsule portion being connected to each other along their respective outer peripheries, and with said anteriorly incomplete capsular bag having predetermined physical or optical properties, or both, and said member further including a plurality of circumferentially distributed artificial zonular fibers made of a biocompatible cross-linked substance and each being attached at one end region thereof to a respective one of said anterior capsular flap portion and said posterior capsule portion in the outer peripheral regions thereof and extending generally radially outwardly of said anteriorly incomplete capsular bag, said artificial zonular fibers being adapted for connection at their other end regions to the ciliary body of the eye, said member thereby being adapted, when implanted into the eye following an intracapsular cataract extraction, to constitute a replacement for the endogenous capsular bag of the eye and to provide a receptacle for an intraocular lens.

11. For use in connection with ophthalmic surgical procedures; a "spare part" adapted to be surgically introduced into an eye for the purpose of repair or reinforcement or replacement of a component of the eye, said "spare part" comprising a member made of a cohesive sheet material of a cross-linked biocompatible substance, said member being preformed to have the shape of an anteriorly incomplete capsular bag which includes a generally circular posterior wall defining a posterior capsule portion and a generally circular substantially centrally apertured anterior wall defining an annular anterior capsular flap portion, with said anterior capsular flap portion and said posterior capsule portion being connected to each other along their respective outer peripheries, and with said anteriorly incomplete capsular bag having predetermined physical or optical properties, or both, and said member further including a built-in intraocular lens constituted by a lens-shaped body having light-refractive properties and secured to a medial region of said posterior capsule portion of said member, said member thereby being adapted, when implanted into the part of the endogenous capsular bag of the eye that remains following an extra-capsular cataract extraction, to constitute a patch for covering and sealing a tear or rent in the endogenous posterior capsule and to automatically provide the implantation of an intraocular lens.

12. For use in connection with ophthalmic surgical procedures; a "spare part" adapted to be surgically introduced into an eye for the purpose of repair or reinforcement or replacement of a component of the eye, said "spare part" comprising a member made of a cohesive sheet material of a cross-linked biocompatible substance, said member being preformed to have the shape of an anteriorly incomplete capsular bag which includes a generally circular posterior wall defining a posterior capsule portion and a generally circular substantially centrally apertured anterior wall defining an annular anterior capsular flap portion, with said anterior capsular flap portion and said posterior capsule portion being connected to each other along their respective outer peripheries, and with said anteriorly incomplete capsular bag having predetermined physical or optical properties, or both, said member further including a built-in intraocular lens constituted by a lens-shaped body having light-refractive properties and secured to a medial region of said posterior capsule portion of said member, and said member further including a plurality of circumferentially distributed artificial zonular fibers made of a biocompatible cross-linked substance and each being attached at one end region thereof to a respective one of said anterior capsular flap portion and said posterior capsule portion in the outer peripheral regions thereof and extending generally radially outwardly of said anteriorly incomplete capsular bag, said artificial zonular fibers being adapted for connection at their other end regions to the ciliary body of the eye, said member thereby being adapted, when implanted in the eye following an intracapsular cataract extraction, to constitute a replacement for the endogenous capsular bag of the eye and to automatically provide the implantation of an intraocular lens.

13. A "spare part" according to claim 11 or 12, wherein said lens-shaped body is adhesively bonded to the anterior surface of said posterior capsule portion.

14. A "spare part" according to claim 11 or 12, wherein said posterior capsule portion of said member has an opening therethrough bounded by a peripheral edge, and said lens-shaped body is located within the confines of said opening and is fused at its periphery to said posterior capsule portion along said peripheral edge of said opening.

15. For use in connection with ophthalmic surgical procedures; a "spare part" adapted to be surgically introduced into an eye for the purpose of repair or reinforcement or replacement of a component of the eye, said "spare part" comprising a member made of a cohesive sheet material of a cross-linked biocompatible substance, said member being preformed to have the shape of an anteriorly incomplete half-capsular bag which includes a posterior wall of generally semi-circular segment shape defining a half-circular posterior capsule portion and an anterior wall of a half-circular ring shape defining a half-annular anterior capsular flap portion having its outer circularly curved periphery connected with the circularly curved periphery of said posterior capsule portion, with said anteriorly incomplete half-capsular bag having predetermined physical or optical properties, or both, said member thereby being adapted, when implanted into the part of the endogenous capsular bag of the eye that remains following an extracapsular cataract extraction, to constitute a patch for covering and sealing a tear or rent in the endogenous posterior capsule and to constitute a part of a receptacle defined by the endogenous posterior capsule for an intraocular lens.

*16. A "spare part" according to claim 1, wherein said posterior capsule portion is provided in its mid-region with an opening which imparts to said posterior capsule portion a curved strip-like configuration.*

*17. A "spare part" according to claim 16, wherein the width of said posterior capsule portion measured radially of said anteriorly incomplete capsular bag-like structure is greater than the corresponding width of said anterior capsular flap portion.*

* * * * *